(12) United States Patent
Preston et al.

(10) Patent No.: US 6,300,075 B1
(45) Date of Patent: Oct. 9, 2001

(54) ENHANCEMENT OF THE SPECIFICITY OF NUCLEIC ACID AMPLIFICATION BY CARRIER NUCLEIC ACID

(75) Inventors: Gregory M. Preston, Salem, CT (US); John W. Backus, Ballwin, MO (US)

(73) Assignee: Ortho-Clinical Diagnostics, INC, Raritan, NJ (US)

( * ) Notice: Subject to any disclaimer, the term of this patent is extended or adjusted under 35 U.S.C. 154(b) by 0 days.

(21) Appl. No.: 09/493,351

(22) Filed: Jan. 28, 2000

Related U.S. Application Data

(60) Provisional application No. 60/118,495, filed on Feb. 3, 1999.

(51) Int. Cl.⁷ .............................. C12Q 1/68; C12P 19/34
(52) U.S. Cl. ................................................ 435/6; 435/91.2
(58) Field of Search .................................. 435/91.2, 91.5

(56) References Cited

U.S. PATENT DOCUMENTS

| | | | |
|---|---|---|---|
| 5,338,671 | 8/1994 | Scalice et al. ..................... | 435/91.2 |
| 5,491,086 | 2/1996 | Gelfand et al. ..................... | 435/194 |
| 5,587,287 | 12/1996 | Scalice et al. ..................... | 435/6 |
| 5,646,019 | * 7/1997 | Nielson et al. .................... | 435/91.5 |
| 5,985,619 | * 11/1999 | Sutherland et al. ............... | 435/91.2 |

FOREIGN PATENT DOCUMENTS

| | | |
|---|---|---|
| 0592035 A2 | 1/1993 | (EP) . |
| 624641 | 2/1994 | (EP) . |

OTHER PUBLICATIONS

M. Wiedman et al., "Ligase Chain Reaction (LCR)–Overview and Applications", PCR Methods and Applications, vol. 3, pp. S51–S64 (1994).*
Chou et al.,1992, *Nuc. Acids Res.* 20:1717–1723.
Zon et al., 1991, *Anticancer Drug Design* 6:539.
Olson et al., 1990, *PNAS.* 83:1451.
Yoo et al., 1989, *J. Biol. Chem.* 764:17078.
Eckstein et al., 1985, *Ann. Rev. Biochem.* 54:367.
Matteucci et al., 1981, *J. Am. Chem. Soc.* 103:3185.

* cited by examiner

*Primary Examiner*—Kenneth R. Horlick
*Assistant Examiner*—Teresa Strzelecka
(74) *Attorney, Agent, or Firm*—Darby & Darby

(57) ABSTRACT

Disclosed herein are improved methods for amplifying nucleic acids. The methods encompass a method for increasing the specificity of amplification of a target nucleic acid in an amplification reaction, where the reaction reagents include one or more oligonucleotide amplification primers specific to the target nucleic acid, a target nucleic acid, a nucleic acid polymerase, and one or more magnesium salts, by preparing a primer/carrier mixture comprising one or more oligonucleotide amplification primers and carrier nucleic acid, and contacting the primer/carrier admixture with target nucleic acid, one or more magnesium salts, and nucleic acid polymerase.

36 Claims, No Drawings

ENHANCEMENT OF THE SPECIFICITY OF NUCLEIC ACID AMPLIFICATION BY CARRIER NUCLEIC ACID

This application claims priority under 35 U.S.C. §119(e) to U.S. provisional patent application Ser. No. 60/118,495 filed on Feb. 3, 1999, which is herein incorporated by reference in its entirety.

FIELD OF THE INVENTION

This invention pertains to methods for amplifying nucleic acids, particularly in diagnostic tests for infectious microorganisms.

BACKGROUND OF THE INVENTION

Amplification of nucleic acid sequences using polymerase chain reaction (PCR) requires at least two oligonucleotide amplification primers that hybridize to different sequences within the target nucleic acid. In general, it is desirable to avoid the use of oligonucleotide primers having homologous sequences at their 3' ends. Primers with homologous 3' ends can potentially hybridize to each other, resulting in a variety of amplification artifacts, including primer-dimers.

Hybridization of primers having 3' end complementarity can occur once all of the PCR reaction components have been mixed, but prior to initiation of amplification, through stabilization of primer hybrids at low temperatures due to the presence of magnesium in the reaction mixture. Primer-dimer formation occurs at or below room temperature by extension of the hybridized primers by DNA polymerase. The resulting primer-dimer product will amplify during PCR, competing with target nucleic acid for primers and polymerase. If enough primer-dimer product is formed in the initial phase, subsequent PCR amplification of this product can out-compete the designated target, leading to either (i) a false negative result, i.e., the sample appears to lack a particular sequence when in fact the sequence is present or (ii) a "no-test" results, i.e., no signal is obtained from an internal positive control.

In addition to the primary sequence of the primer sets, the major contributors to primer-dimer formation are: a high molar level of primers in the assay specific master mix (ASMM); the order of addition of reactants (for example, adding the ASMM, then $MgCl_2$ solution, then target/sample will increase primer-dimer formation); the incubation period between addition of $MgCl_2$ to the ASMM and addition of target; and the time period during which a complete amplification reaction admixture, i.e., comprising all the components required for amplification, including target and polymerase, incubates prior to initiation of PCR thermocycling.

Several approaches are known to reduce primer-dimer formation in a nucleic acid amplification admixture of primers and polymerase. These approaches include:

1. Carefully designing the PCR primers to minimize 3'-end homologies with all other primers in a particular reaction mixture. However, this strategy is difficult in a multiplex reaction, i.e., a reaction containing several pairs of amplification primers directed to different target nucleic acid sequences. Furthermore, even with a single pair of primers, this may be difficult to achieve, due to other constraints, such as, e.g., regions of identity or conservation.
2. Performing the thermal cycling/amplification reaction soon after preparing an assay-specific reaction admixture to reduce the amount of time available for primer-dimer formation. However, this can be difficult in practice, particularly if large numbers of samples are to be screened.
3. Changing the order of reagent addition to destabilize potential primer-dimers. For example, adding $MgCl_2$ as the last component can reduce primer-dimer formation. This approach, however, is not desirable because (i) it does not eliminate primer-dimer formation, (ii) it is inconvenient, and (iii) it can result in contamination of the magnesium chloride solution with target from a sample.
4. Using "triggering" antibodies, which are antipolymerase antibodies that block polymerase activity at temperatures where primer-hybrids may form, but which are inactivated at high temperatures. Thus, polymerase is only activated at temperatures that are too high for primer-dimers to form. (See, U.S. Pat. Nos. 5,338,671 and 5,587,287; and European Patent Application No. 0592035). However, since antibody/polymerase binding is an equilibrium process, complete binding of all polymerase cannot be achieved. Thus, antibody-based PCR triggering is not necessarily 100% effective, particularly in complex amplification reactions.
5. Performing Hot Start PCR (Chou et al., *Nuc. Acids Res.* 20:1717–1723, 1992). This involves adding everything except the thermostable DNA polymerase to the reaction admixture, initiating the reaction with a product denaturation step, followed by opening up the reaction tubes and adding the polymerase to the reaction admixture. Although this method is effective at reducing primer-dimer formation, it is not practical for a number of reasons. Most notably, it is very cumbersome and significantly increases the likelihood of amplicon carryover.
6. Performing Hot Start PCR using a thermostable DNA polymerase, such as AmpliTaq Gold, that is relatively inactive until heating (See, European Patent application No. 624641 and U.S. Pat. No. 5,491,086). However, AmpliTaq Gold retains significant residual enzyme activity at low temperatures, and thus is still prone to generating side products.

None of these approaches is predictably successful at eliminating primer-dimer formation. Careful primer design and the use of AmpliTaq Gold or triggering antibodies in combination with Taq Polymerase can reduce primer-dimer formation, but does not eliminate it. Thus, there is a need in the art for improved methods for reducing further or eliminating primer-dimer formation in PCR reactions, particularly in multiplex reactions.

SUMMARY OF THE INVENTION

The present invention provides methods for increasing the specificity of amplification of a target nucleic acid. It can be applied to all reactions requiring oligonucleotide amplification primers specific to the target and a nucleic acid polymerase. Thus, in one aspect the invention is directed to a method for increasing the specificity of amplification of a target nucleic acid in an amplification reaction, where the amplification reaction mixture comprises one or more oligonucleotide amplification primers specific to the target, a nucleic acid polymerase, and one or more magnesium salts, comprising preparing a primer-carrier admixture containing one or more primers and carrier nucleic acid, and contacting the primer-carrier admixture with the target nucleic acid, one or more magnesium salts, and polymerase.

In another aspect, the invention is directed to a method for increasing specificity of amplification of a target nucleic acid in an amplification reaction, where the amplification reaction mixture comprises one or more oligonucleotide amplification primers specific to the target nucleic acid, Taq polymerase, and magnesium chloride, comprising preparing a primer-carrier admixture including one or more primers and carrier nucleic acid including calf thymus DNA, where the concentration of the carrier nucleic acid will range from about 1 to about 100 micrograms/ml of amplification reaction mixture, and contacting, at a temperature less than about 100° C., the primer-carrier admixture with the target nucleic acid, Taq polymerase; and magnesium chloride.

In yet another aspect, the invention is directed to a method for reducing polymerize extension of non-target nucleic acids in a reaction for the amplification of a target nucleic acid, where the amplification reaction mixture comprises one or more oligonucleotide amplification primers specific to the target nucleic acid, polymerase, and one or more magnesium salts, comprising preparing an oligonucleotide primer-carrier nucleic acid admixture containing one or more amplification primers and carrier nucleic acid, and contacting the primer-carrier mixture with the target nucleic acid, polymerase, and magnesium salts.

In a fourth aspect, the invention is directed to a method for reducing the formation of primer-dimer or other non-specific nucleic acid amplification products in a reaction for the amplification of a target nucleic acid, where the amplification reaction mixture comprises one or more oligonucleotide amplification primers specific to the target, polymerase, and one or more magnesium salts, comprising preparing a primer-carrier nucleic acid admixture containing one or more primers and carrier nucleic acid, and contacting the the primer-carrier mixture with target nucleic acid, polymerase, and magnesium salts.

Any nucleic acid may be used as a carrier nucleic acid, including DNA, RNA, and protein nucleic acid. Preferably, the carrier is DNA, and, most preferably, calf thymus DNA. Typically, the carrier is added so that the concentration in the final amplification reaction mixture is between about 1 and about 100 $\mu$g/ml, preferably between about 5 and about 75 $\mu$g/ml, and most preferably between about 25 and about 50 $\mu$g/ml.

The methods of the present invention are particularly advantageous in reducing polymerase extension of non-target nucleic acid during amplification assays. The method is particularly applicable when an amplification reaction mixture is maintained at temperatures less than those required to denature the target nucleic acid (i.e., less than 100° C.) prior to initiation of the amplification reaction. Such conditions include, e.g., maintenance of amplification reaction mixtures at room temperature or slightly below room temperature for from about 1 to about 24 hours.

DETAILED DESCRIPTION OF THE INVENTION

The present invention is based on the finding that adding carrier nucleic acid to a nucleic acid amplification mixture considerably increases the efficiency and specificity of amplification of the target nucleic acid. Specifically, the method of the invention results in a reduction in polymerase extension of non-target nucleic acids during amplification assays through a reduction in the amount of primer-dimer formation prior to raising the temperature of the amplification mixture during thermal cycling.

Many techniques in molecular biology, microbiology, recombinant DNA, and protein biochemistry are used in practicing the present invention, such as those explained in, for example, Sambrook et al., 1989, *Molecular Cloning: A Laboratory Manual,* Second Edition, Cold Spring Harbor Laboratory Press, Cold Spring Harbor, N.Y.; *DNA Cloning: A Practical Approach,* Volumes I and II, 1985 (D. N. Glover ed.); *Oligonucleotide Synthesis,* 1984, (M. L. Gait ed.); *Transcription and Translation,* 1984 (Hames and Higgins eds.); *A Practical Guide to Molecular Cloning;* the series, *Methods in Enzymology* (Academic Press, Inc.); and *Protein Purification: Principles and Practice,* Second Edition (Springer-Verlag, N.Y.).

Amplification reaction mixture as used herein refers to the amplification-competent admixture of at least amplification primers, target nucleic acid, deoxynucleotides, polymerase, one or more magnesium salts, and buffers, in amounts sufficient quantities to allow a nucleic acid amplification reaction to proceed.

"Nucleic acid" or "polynucleotide" as used herein refers to purine- and pyrimidine-containing polymers of any length, either polyribonucleotides or polydeoxyribonucleotides or mixed polyribo-polydeoxyribo nucleotides. This includes single- and double-stranded molecules, such as, for example, DNA-DNA, DNA-RNA and RNA-RNA hybrids, as well as "protein nucleic acids" (PNA) formed by conjugating bases to an amino acid backbone. This also includes nucleic acids containing modified bases.

A "complement" of a nucleic acid sequence as used herein refers to the antisense sequence that participates in Watson-Crick base-pairing with the original sequence.

A "primer" as used herein is an oligonucleotide between about 6 and about 50 nucleotides in length, preferably between about 12 and about 25 nucleotides in length and most preferably between about 12 and about 18 nucleotides in length, that forms a duplex with a single-stranded nucleic acid sequence of interest and allows polymerization of a complementary strand using, e.g., reverse transcriptase or DNA polymerase.

Amplification as used herein refers to an iterative process by which a nucleic acid is copied. Suitable methods for amplification include without limitation polymerase chain reaction, ligase chain reaction, strand displacement amplification, nucleic acid single base amplification, and transcription mediated amplification.

A "target nucleic acid" as used herein refers to a nucleic acid template, a subsequence of which is amplified during a PCR reaction.

An internal positive control (IPC) target nucleic acid is a synthetic nucleic acid sequence cloned into a plasmid vector which is subsequently linearized, typically by the action of a restriction endonuclease. An IPC will typically have multiple primer binding sequences surrounding a generic probe-binding region, and acts as a generic control against false negative results in nucleic acid amplification reactions.

The sequence of a preferred internal positive control target DNA is:
5'-CGCCAGCGTGGACCATCAAGTAGTAATGAACG-
CACGGACGAGGACATCATAGAGATTA-
CACCTTTATCCACAGTTCTCG-
GTCTAACGCAGCAGTCAGTG
TATCAGCACCAGCATCCGTAGTGAGTCTTCAG-
TGTCTGCTCCAGG- ATCGT G-3'<SEQ ID NO: 1>.

The present invention can be applied to any reaction in which one or more oligonucleotides are incubated with a target nucleic acid in order to hybridize to the target nucleic acid and prime the enzymatic replication of the target nucleic acid. Such reactions include, e.g., polymerase chain reaction (PCR), ligase chain reaction, strand displacement amplification, nucleic acid single base amplification, and transcription mediated amplification.

In these reactions, an assay-specific master mix is formulated, containing the oligonucleotide primers, buffers and salts, deoxynucleotides, and, optionally, other components. The target nucleic acid is then added, followed by the enzyme, e.g., Taq polymerase, that catalyzes the reaction and/or a magnesium salt, e.g., magnesium chloride, that is essential for the progression of the reaction.

Other components suitable for use in the methods of the present invention include without limitation anti-polymerase antibodies which bind to and inactivate polymerase low temperatures, but which are themselves inactivated at high temperatures, thus allowing activation of polymerase at high temperatures. Exonucleases and glycosylases can also be included in the reaction mixture.

In practicing the present invention, the oligonucleotide primers are contacted with carrier nucleic acid prior to mixing with the target nucleic acid, polymerase, or magnesium salts.

Carrier nucleic acid according to the invention may comprise any nucleic acid, including, without limitation, prokaryotic or eukaryotic DNA and/or RNA, synthetic DNA and/or RNA, or random and/or specific PNA (peptide nucleic acid). Preferably, the carrier comprises DNA, and most preferably calf thymus DNA.

Carrier nucleic acids for use in the invention can be prepared by conventional methods. For example, DNA or RNA can be isolated from cells by deproteinization. DNA can be chemically synthesized using, e.g., the phosphoramidite solid support method of Matteucci et al., 1981, *J. Am. Chem. Soc.* 103:3185, the method of Yoo et al., 1989, *J. Biol. Chem.* 764:17078, or other well known methods. The nucleic acids utilized in the invention may also be modified by any means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) or charged linkages (e.g., phosphorothioates, phosphorodithioates, etc.). Nucleic acids may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The nucleic acid may be derivatized by formation of a methyl or ethyl phosphotriester or an alkyl phosphoramidate linkage. Thiolated amplification primers, where one or more oxygen atoms of a phosphate group are replaced with a sulfur atom, can be synthesized by, e.g., methods described by Eckstein et al., *Ann. Rev. Biochem.* 54:367 (1985); Zon et al., *Anticancer Drug Design* 6:539 (1991); and Olson et al., *PNAS* 83:1451 (1990).

The carrier nucleic acid is added to the primer-containing master mix in a quantity sufficient so that the final concentration of carrier nucleic acid in the amplification reaction volume ranges between about 1 and about 100 $\mu$g/ml, preferably between about 5 and about 75 $\mu$g/ml, and most preferably about 25 to about 50 $\mu$g/ml. Typical amounts of primer in the reaction are concentrations ranging from about 0.1 $\mu$M to about 1 $\mu$M. The optimal amount of carrier may be determined independently for a particular assay. This determination can be achieved by adding increasing amounts of a carrier nucleic acid to a standardized master mix, adding the target nucleic acid and enzyme, and, following the reaction, monitoring the level of specific and non-specific amplification products. (See, e.g., Example 1 below).

The carrier nucleic acid is preferably admixed with the oligonucleotide primers prior to addition of the target nucleic acid. The primer-carrier mixture is then admixed with target nucleic acid, polymerase which catalyzes the amplification reaction and a magnesium salt which is essential to the efficient function of the polymerase. Typically, the reaction mixture is maintained at a temperature less than about 90 to about 100° C. prior to initiation of the amplification reaction. Preferably, the amplification is conducted by thermal cycling, and the temperature of the admixture is maintained at less than about 90 to about 100° C. prior to initiating thermal cycling. Most preferably, the reaction mixture is maintained at about room temperature prior to initiating the amplification reaction.

Without wishing to be bound by theory, it is believed that reduction of primer-dimer formation occurs by several different mechanisms. First, polymerase binds to the carrier nucleic acid. This is particularly beneficial when anti-polymerase antibodies are also present in the admixture, as polymerase molecules that are not bound by anti-polymerase antibodies are bound to carrier nucleic acid, thus further reducing the likelihood of extension of any hybridized primers that may be present. Second, the carrier nucleic acid is believed to reduce the number of hybridized primers in the admixture since the primers will also anneal weakly to carrier DNA. Non-specific extension products formed from binding of primers to carrier nucleic acid will not be amplified during the target amplification phase of the PCR, as paired primers for these non-specific sites are not present. Thus, primer-dimer formation (and formation of other non-specific nucleic acid product) is reduced.

DESCRIPTION OF THE PREFERRED EMBODIMENTS

The following examples are intended to illustrate the present invention without limitation.

EXAMPLE 1

Effect of Carrier Nucleic Acid on PCR Amplification of HIV Sequences

The following experiments were performed to monitor the effect of adding carrier nucleic acid to an HIV amplification reaction.

A master mix was formulated which contained the eleven primers shown in Table 1, Tris buffer, dNTPs, AmpliTaq, and two AmpliTaq triggering antibodies (U.S. Pat. Nos. 5,338,671 and 5,587,287; European Patent No. 0592035). Master mixes were prepared without and with calf thymus DNA (group I and group II, respectively).

TABLE 1

| | Final Concentration | Primer Sequence |
|---|---|---|
| IPC-F1 | 0.2 $\mu$M | 5'-CGC CAG CGT GGA CCA TCA AGT AGT AA-3' <SEQ ID NO.: 2>. |

TABLE 1-continued

| Primer | Final Concentration | Sequence |
|---|---|---|
| IPC-R1 | 0.2 µM | 5'-CAC GAT CCT GGA GCA GAC ACT GAA GA-3' <SEQ ID NO.: 3>. |
| JBPOL1 | 0.4 µM | 5'-TCG GGT TTA TTA CAG GGA CAG CAG AGA-3'<SEQ ID NO.: 4>. |
| JBPOL3 | 0.4 µM | 5'-CTT GTA TTA CTA CTG CCC CTT CAC CTT TCC A-3'<SEQ ID NO.: 5>. |
| JBLTR4 | 0.4 µM | 5'-CTG CTT AAG CCT CAA TAA AGC TTG CCT TGA-3'<SEQ ID NO.: 6>. |
| JBLTR6 | 0.4 µM | 5'-GGG TCT GAG GGA TCT CTA GTT ACC AGA GT-3'<SEQ ID NO.: 7>. |
| JBLTR8 | 0.4 µM | 5'-TGT TCG GGC GCC ACT GCT AGA GA-3'<SEQ ID NO.: 8>. |
| 2ENV-F1 | 0.4 µM | 5'-CCG GGA TAG TGC AGC AAC AGC AAC A-3' <SEQ ID NO.: 9>. |
| 2ENV-R2 | 0.4 µM | 5'-CCC AGA CGG TCA GTC GCA ACA-3'<SEQ ID NO.: 10>. |
| 2LTRe | 0.4 µM | 5'-GGG AGG TTC TCT CCA GCA CTA GCA-3' <SEQ ID NO.: 11>. |
| 2LTR-R1 | 0.4 µM <SEQ ID NO.: 12>. | 5'-GCG ACT AGG AGA GAT GGG AAC ACA CA-3' |

To 50 µl aliquots of Group I and Group II master mixes was added 25 µl of 16 mM MgCl₂ followed by 25 µl target mix (containing 13.3 copies of Internal positive control target nucleic acid in 20 mM NaOH). For each group, three different experimental protocols were employed, which are shown in Table 2 below.

TABLE 2

| Group | 1st Reagent Addition | Incubation | 2nd Reagent Addition | Incubation |
|---|---|---|---|---|
| I-a | ASMM-1, MgCl₂, Target | 1 hour | — | |
| I-b | ASMM-1, MgCl₂, Target | 4 hours 20 min. | — | |
| I-c | ASMM-1, MgCl₂ | 4 hours | Target | 20 min. |
| II-a | ASMM-2, MgCl₂, Target | 1 hour | — | |
| II-b | ASMM-2, MgCl₂, Target | 4 hours 20 min. | — | |
| II-c | ASMM-2, MgCl₂ | 4 hours | Target | 20 min. |

I (a,b,c) = No Carrier DNA in master mix
II (a,b,c) = Carrier (calf thymus) DNA in master mix In one set of reaction mixtures, designated A, the IPC primers were non-thiolated, while in a second set, designated B, the IPC primers were thiolated.

All reactions were performed in duplicate. 75 µl aliquots of the mixtures were added to blank nucleic acid pouches (Ortho Clinical Diagnostics, Rochester, N.Y.). PCR amplification conditions were as follows:

(1) 96° C. for 3 min to completely denature the DNA and the AmpliTaq triggering antibodies;
(2) 5 cycles of 96° C. for 5 sec followed by 62° C. for 40 sec;
(3) 35 cycles of 96° C. for 5 sec followed by 68° C. for 40 sec.

Amplification products were removed from the pouches and resolved by electrophoresis on 4% agarose gels in Tris-boric acid buffer. Amplified DNA product was detected using ethidium bromide staining.

The results of the experiment were assessed by visual inspection of the intensity of both specific (IPC) and non-specific products (primer-dimer and other false priming products) in photographs of the gels (Table 3). Specific and nonspecific product band intensities were assessed visually on a scale from 0–10, where 0 represents the absence of a detectable band, and a '10' represents maximum Intensity. NA, not assayed.

TABLE 3

| | | Part A: with non-Thio IPC primers. | | Part B: with Thiolated IPC primers. | |
|---|---|---|---|---|---|
| Group | Rep # | Specific Product Band Intensity | Non-specific Product Band Intensity | Specific Product Band Intensity | Non-specific Product Band Intensity |
| I-a | 1 | NA | NA | NA | NA |
| I-a | 2 | 6 | 2 | 7 | 2 |
| I-b | 1 | 5 | 3 | 7 | 3 |
| I-b | 2 | 6 | 2 | 7 | 2 |
| I-c | 1 | 0 | 8 | 1 | 9 |
| I-c | 2 | 1 | 9 | 0 | 10 |
| II-a | 1 | 8 | 0 | 7 | 0 |
| II-a | 2 | 7 | 1 | 8 | 1 |
| II-b | 1 | 7 | 2 | 9 | 1 |
| II-b | 2 | 7 | 1 | 9 | 0 |
| II-c | 1 | 6 | 3 | 8 | 3 |
| II-c | 2 | 6 | 3 | 8 | 1 |

In all three subsets (a–c), the group II amplification reactions produced stronger specific product bands and weaker non-specific product bands compared with group I. This was true for part A of the experiment (which employed non-thiolated IPC primers) as well as in part B of the experiment (which employed thiolated IPC primers). In all four groups, primer-dimer product levels increased and specific product levels decreased as the admixture was subjected to conditions increasingly favorable to primer-dimer formation (a–c), including incubation of the admixture at room temperature for approximately 4 hours prior to thermocycling. In I-c, the only visible gel bands were intense primer-dimer bands. In contrast, intense product bands were seen in II-c reactions with proportionately very little primer-dimer product. Finally, although IPC primer thiolation (part B) resulted in slightly increased specific product synthesis, this was not nearly as beneficial as a master mix formulation with carrier nucleic acid.

All patents, applications, articles, publications, and test methods mentioned herein are hereby incorporated by reference in their entirety.

Many variations of the present invention will suggest themselves to those skilled in the art in light of the above detailed description. Such obvious variations are within the full intended scope of the appended claims.

What is claimed is:

1. A method for increasing the specificity of amplification of a target nucleic acid in an amplification reaction, said method comprising:
   (a) contacting one or more oligonucleotide amplification primers and carrier nucleic acid so that a primer/carrier admixture is formed; and
   (b) contacting said primer/carrier admixture with target nucleic acid, one or more magnesium salts, and nucleic acid polymerase so that the target nucleic acid is amplified,
   wherein formation of the primer carrier admixture before amplifying the target nucleic acid increases the specificity of amplification.

2. A method as defined in claim 1, wherein said carrier nucleic acid is selected from the group consisting of DNA, RNA, and peptide nucleic acid (PNA).

3. A method as defined in claim 2, wherein said DNA is calf thymus DNA.

4. A method as defined in claim 1, wherein said carrier nucleic acid is present in said amplification reaction at a concentration ranging from about 1 to about 100 micrograms per ml.

5. A method as defined in claim 4, wherein said carrier nucleic acid is present in said amplification reaction at a concentration ranging from about 5 to about 75 micrograms per ml.

6. A method as defined in claim 1, wherein said admixture is maintained at a temperature less than about 90 to about 100° C. prior to initiation of the amplification reaction.

7. A method as defined in claim 6, wherein said temperature is maintained prior to initiating thermal cycling.

8. A method as defined in claim 1, wherein said polymerase comprises Taq polymerase.

9. A method as defined in claim 1, wherein said magnesium salts comprise magnesium chloride.

10. A method as defined in claim 1, wherein said admixture further comprises a member selected from the group consisting of anti-polymerase antibody, an exonuclease, a glycosylase, or any combination thereof.

11. A method for increasing the specificity of amplification of a target nucleic acid in an amplification reaction, the method comprising:
    (a) contacting one or more primers and carrier nucleic acid comprising calf thymus DNA, so that a primer-carrier admixture is formed; and
    (b) contacting said primer-carrier admixture with target nucleic acid, Taq polymerase, and magnesium chloride so that the target nucleic acid is amplified;
    wherein the concentration of the carrier nucleic acid in said amplification reaction ranges from about 1 to about 100 micrograms/ml of amplification reaction volume, and
    wherein formation of the primer-carrier admixture before amplifying the target nucleic acid increases the specificity of amplification.

12. A method for reducing polymerase extension of non-target nucleic acids in a reaction for the amplification of a target nucleic acid, the method comprising:
    (a) contacting one or more amplification primers and carrier nucleic acid so that a primer-carrier nucleic acid admixture is formed; and
    (b) contacting said primer-carrier admixture with target nucleic acid, polymerase, and one or more magnesium salts so that the target nucleic acid is amplified,
    wherein formation of the primer-carrier admixture before amplifying the target nucleic acid reduces polymerase extension of non-target nucleic acids.

13. A method as defined in claim 12, wherein said carrier nucleic acid is selected from the group consisting of DNA, RNA, and peptide nucleic acid (PNA).

14. A method as defined in claim 13, wherein said DNA is calf thymus DNA.

15. A method as defined in claim 12, wherein said carrier nucleic acid is present in said amplification reaction at a concentration ranging from about 1 to about 100 micrograms per ml.

16. A method as defined in claim 15, wherein said carrier nucleic acid is present in said amplification reaction at a concentration ranging from about 5 to about 75 micrograms per ml.

17. A method as defined in claim 16, wherein said admixture is maintained at a temperature less than about 90 to about 100° C. prior to initiation of the amplification reaction.

18. A method as defined in claim 17, wherein said temperature is maintained prior to initiating thermal cycling.

19. A method as defined in claim 12, wherein said polymerase comprises Taq polymerase.

20. A method as defined in claim 12, wherein said magnesium salts comprise magnesium chloride.

21. A method as defined in claim 12, wherein said admixture further comprises a member selected from the group consisting of anti-polymerase antibody, an exonuclease, a glycosylase, or any combination thereof.

22. A method for reducing the formation of non-specific nucleic acid amplification products in a reaction for the amplification of a target nucleic acid, the method comprising:
    (a) contacting one or more primers and carrier nucleic acid so that a primer-carrier admixture is formed; and
    (b) contacting said target nucleic acid with said primer-carrier mixture;
    wherein said primer-carrier admixture is prepared prior to contacting said primers with a member selected from the group consisting of polymerase, one or more magnesium salts, and mixtures thereof so that the formation of non-specific nucleic acid amplification products is reduced.

23. A method as defined in claim 22, wherein said carrier nucleic acid is selected from the group consisting of DNA, RNA, and peptide nucleic acid (PNA).

24. A method as defined in claim 23, wherein said carrier nucleic acid is DNA.

25. A method as defined in claim 24, wherein said DNA is calf thymus DNA.

26. A method as defined in claim 22, wherein said carrier nucleic acid is present in said amplification reaction at a concentration ranging from about 1 to about 100 micrograms per ml.

27. A method as defined in claim 26, wherein said carrier nucleic acid is present in said amplification reaction at a concentration ranging from about 5 to about 75 micrograms per ml.

28. A method as defined in claim 22, wherein said admixture is maintained at a temperature less than about 90 to about 100° C. prior to initiation of the amplification reaction.

29. A method as defined in claim 28, wherein said temperature is maintained prior to initiating thermal cycling.

30. A method as defined in claim 22, wherein said polymerase comprises Taq polymerase.

31. A method as defined in claim 22, wherein said magnesium salts comprise magnesium chloride.

32. A method as defined in claim 22, wherein said admixture further comprises a member selected from the group consisting of anti-polymerase antibody, a buffer, a deoxynucleotide triphosphate, an exonuclease, a glycosylase, or any combination thereof.

33. A method as defined in claim 6, wherein said temperature is about room temperature.

34. A method as defined in claim 17, wherein said temperature is about room temperature.

35. A method as defined in claim 28, wherein said temperature is about room temperature.

36. A method according to claim 32, wherein the non-specific nucleic acid amplification product comprises one or more primer-dimers.

* * * * *

```
                              SEQUENCE LISTING

<160> NUMBER OF SEQ ID NOS: 12

<210> SEQ ID NO 1
<211> LENGTH: 150
<212> TYPE: DNA
<213> ORGANISM: Artificial Sequence
<220> FEATURE:
<223> OTHER INFORMATION: Oligonucleotide primer

<400> SEQUENCE: 1
cgccagcgtg gaccatcaag tagtaatgaa cgcacggacg aggacatcat agagattaca      60
cctttatcca cagttctcgg tctaacgcag cagtcagtgt atcagcacca gcatccgtag     120
tgagtcttca gtgtctgctc caggatcgtg                                     150

<210> SEQ ID NO 2
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 2
cgccagcgtg gaccatcaag tagtaa                                          26

<210> SEQ ID NO 3
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 3
cacgatcctg gagcagacac tgaaga                                          26

<210> SEQ ID NO 4
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 4
tcgggtttat tacagggaca gcagaga                                         27

<210> SEQ ID NO 5
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 5
cttgtattac tactgcccct tcacctttcc                                      30

<210> SEQ ID NO 6
<211> LENGTH: 30
<212> TYPE: DNA
<213> ORGANISM: Artificial Sequence
<220> FEATURE:
<223> OTHER INFORMATION: Oligonucleotide primer
```

```
<400> SEQUENCE: 6
ctgcttaagc ctcaataaag cttgccttga                              30

<210> SEQ ID NO 7
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 7
gggtctgagg gatctctagt taccagagt                               29

<210> SEQ ID NO 8
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 8
tgttcgggcg ccactgctag aga                                     23

<210> SEQ ID NO 9
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 9
ccgggatagt gcagcaacag caaca                                   25

<210> SEQ ID NO 10
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 10
cccagacggt cagtcgcaac a                                       21

<210> SEQ ID NO 11
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 11
gggaggttct ctccagcact agca                                    24

<210> SEQ ID NO 12
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 12
gcgactagga gagatgggaa cacaca                                  26
```